United States Patent
Wang et al.

(10) Patent No.: US 9,499,552 B2
(45) Date of Patent: Nov. 22, 2016

(54) PYRAZOLO[1,5-A]PYRIMIDINE DERIVATIVE AND USE OF ANTI-TUMOR THEREOF

(71) Applicant: YANTAI UNIVERSITY, Yantai (CN)

(72) Inventors: Hongbo Wang, Yantai (CN); Xuechuan Hong, Wuhan (CN); Xi Zhu, Wuhan (CN); Mingmin Ding, Wuhan (CN); Guangyao Lv, Yantai (CN); Jianqiao Zhang, Yantai (CN); Meng Wen, Wuhan (CN); Chunrong Qu, Wuhan (CN); Jinmei Zhu, Wuhan (CN); Xianming Hu, Wuhan (CN)

(73) Assignees: Yanti University, Yanti (CN); Wuhan University, Wuhan (CN)

( * ) Notice: Subject to any disclaimer, the term of this patent is extended or adjusted under 35 U.S.C. 154(b) by 0 days.

(21) Appl. No.: 14/719,971

(22) Filed: May 22, 2015

(65) Prior Publication Data

US 2016/0102095 A1 Apr. 14, 2016

(30) Foreign Application Priority Data

Oct. 9, 2014 (CN) .......................... 2014 1 0532741

(51) Int. Cl.
*C07D 487/04* (2006.01)
*C07D 519/00* (2006.01)

(52) U.S. Cl.
CPC .................................. *C07D 487/04* (2013.01)

(58) Field of Classification Search
CPC .......................... C07D 487/04; C07D 519/00
See application file for complete search history.

(56) References Cited

U.S. PATENT DOCUMENTS

2009/0163545 A1* 6/2009 Goldfarb .............. A61K 31/122
514/312

* cited by examiner

*Primary Examiner* — Alexander R Pagano
*Assistant Examiner* — Ebenezer O Sackey
(74) *Attorney, Agent, or Firm* — Ladas & Parry LLP

(57) ABSTRACT

The present invention relates to a pyrazolo[1,5-a]pyrimidine derivative of general formula 1 and a pharmaceutically acceptable salt thereof. The present invention also relates to use of compounds of formula 1 in the preparation of an anti-tumor medicament.

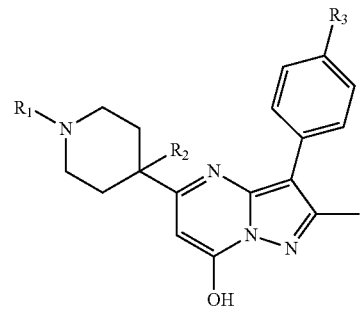

3 Claims, 2 Drawing Sheets

Figure 1

F: Fluorescence after administration; F₀: Fluorescence without administration

RFU = Relative Fluorescence Unit

PYRAZOLO[1,5-A]PYRIMIDINE DERIVATIVE AND USE OF ANTI-TUMOR THEREOF

TECHNICAL FIELD

The present invention belongs to the field of organic synthesis, and relates to a anti-tumor drug Pyrazolo[1,5-a]pyrimidine derivative and use thereof.

BACKGROUND

With the extension of human life, cancer emerged as the leading cause of death in recent years. "2012 Chinese Cancer Registry Annual Report" shows that about 3.5 million of new cancer cases occur and about 2.5 million of persons die of cancer each year in China. Lung cancer has a highest incidence among malignant tumors in China, followed by stomach cancer, colorectal cancer, liver cancer and esophageal cancer. Cancer has become the leading cause of human death in China.

With regard to treatment of cancers, scientists have carried out a lot of research work. New anticancer drugs are discovered continuously. Currently, there are more than 20 kinds of cancers, cure rates of which are above 30%. The research of drug action mechanism at sub-cellular and molecular level largely expands the research in the application of anti-cancer drugs. The rapid development of cell kinetics, pharmacokinetics and immunological research makes the drug screening, dose titeration, and determination of route of administration become more and more mature. Now treatments of malignant tumors have achieved very good therapeutic effects by means of combination therapy, high-dose intermittent therapy, adjuvant chemotherapy, and therapy in combination with traditional Chinese medicine. Nowadays the means for treatment of cancer are mainly surgery therapy, radiation therapy, chemotherapy, traditional Chinese medicine therapy and immunotherapy etc. The choice of anti-cancer drugs, toxicity and drug resistance etc. affect the efficacy since the anti-cancer drugs can kill not only tumor cells, but also cells of normal tissues, especially quickly proliferative hematopoietic cell in bone marrow and stomach intestinal cells. This limits doses of anti-cancer drugs, and reduces immune function in patients. Worse still, it can result in the failure of the treatment as a result of the unbearable gastrointestinal reactions which force the patients to discontinue the treatment. Anti-cancer drugs can kill cancer cells, but also have cytotoxicity. So, it is always the goal of scientists to find a drug which can treat cancer and have no or little harm to human. Recently, researches on the relationship between TRPC6 protein as one member of subfamily of transient receptor potential channels and the change of intracellular calcium concentration, development of tumor, changes of tumor cell cycle has made new progress. TRPC6 is expected to become a new target for cancer therapy.

Transient receptor potential channel (TRPC) is a non-selective cation channel protein family commonly found in the cell membrane, and plays an important role in mediating sensory conduction, cell signal transduction and regulation of development etc. Currently, it is one of hotspots in research field of ion channels. TRP channel proteins are a large family, and are widely expressed in a variety of organisms, tissues and cells. As far as mammalian TRP channels are concerned, this family includes seven interrelated sub-families: TRPC, TRPV, TRPM, TRPN, TRPA, TRPP and TRPML, each of which in turn comprises a number of family members. The previous research on TRP ion channels was restricted to the nervous system. Recent studies have shown that TRP channels play an important role not only in cellular signal transduction, mediating nociception etc. in the body, but also in tumor occurrence and development. The family has a stabilizing and regulating effect on cells, its increased expression promotes growth of malignant tumors.

TRPCs, namely the traditional TRP channel, are the first TRP channel proteins which are isolated and researched. TRPC has 7 subtypes, namely TRPC (1~7), wherein TRPC3 and TRPC6 are very similar in structure and function, and the identity of amino acids is as high as 70%-80%. Besides, their pharmacological properties and signal regulating functions are also similar. They are more representative in TRPC subfamily, and are two subtypes concerned in the current international research. And TRPC6 is considered as the most selective channel protein. Human TRPC6 locates on chromosome 11q212q22, has a total of 132,287 bases (gene pool: NC000011), and contains 13 exons. The mRNA as transcription product of TRPC6 contains 4,564 bases, wherein the 1-427 positions are 5' untranslated region, the 428-3,223 positions are coding region, the 3,224-4,564 positions are 3' untranslated region (gene pool: NM004621). TRPC6 can be specifically activated by phospholipase C (PLC), subsequently lead the ligand to bind to the membrane receptor by G-protein coupled receptor (GPCR) mediated signal transduction pathway, then activate phospholipase C to generate 1,4,5-inositol triphosphate, which binds to a receptor to promote the $Ca^{2+}$ release from the endoplasmic reticulum. TRPC6 is a non-selective cation channel through which calcium ions can pass, and is expressed in many tissues. It can directly be activated by the second messenger diacylglycerol enzymes, subsequently intracellular calcium flux is changed by phosphorylation regulation of particular tyrosine/serine. The increase of intracellular free $Ca^{2+}$ activates some protein phosphatases, resulting in the phosphorylation of substrate proteins. The external signals are enlarged by cascade amplification, then enter the nucleus and affect the DNA replication, leading to malignant transformation of cells as well as proliferation and differentiation of tumor cells. Intracellular $Ca^{2+}$ directly involves in the regulation of growth, invasion, metastasis, and differentiation of tumors. Therefore, TRPC6 inhibitors are expected to become new drugs to treat cancer. However, there are few reports about TRPC6 inhibitors.

In recent years, scientists have conducted a series of studies on the relationship between TRPC6 and human tumors. The results demonstrate that TRPC6 is closely associated with the higher incidence of gastric cancer, liver cancer, esophageal cancer and so on. David G. W. reported the TRPC3 and TRPC6 inhibitors in 2013. The compounds synthesized by them have $IC_{50}$ values that can reach nanomolar order for hTRPC3 and hTRPC6. However, as for animal experiments, the series of drugs were found to have low oral bioavailability and unduly high in vivo clearance rate. Even after a series of structural modification, the people still cannot find a balance point to make both the activity and oral bioavailability arrive at a good level.

Through a large number of screening, we found that compound 1 has excellent TRPC6 inhibitory effect and is a potential antitumor drug.

CONTENTS OF THE INVENTION

The present invention aims to provide a pyrazolo[1,5-a]pyrimidine derivative. The present invention also provides activity screening results of said compounds at cellular level and target level and the antitumor use thereof.

The present invention relates to a pyrazolo[1,5-a]pyrimidine derivative having the structure as shown in general formula 1:

1 wherein:
R$_1$ is hydrogen, alkylcarbonyl, alkoxycarbonyl, alkylthiocarbonyl;
R$_2$ is hydrogen, alkyl, haloalkyl;
R$_3$ is hydrogen, halogen, trifluoromethyl;
said alkyl is C$_1$-C$_6$ linear, branched or cyclic alkyl group such as methyl, ethyl, n-propyl, isopropyl, n-butyl, cyclohexyl and the like;
said haloalkyl is a haloalkyl substituted by 1-5 halogen atoms, such as a monochloromethyl, trifluoroethyl and the like;
said alkoxycarbonyl is a C$_1$-C$_6$ alkoxycarbonyl, such as methoxycarbonyl, ethoxycarbonyl, t-butoxycarbonyl group and the like;
said alkylcarbonyl is a C$_1$-C$_6$ alkylcarbonyl group, such as formyl, acetyl, propionyl, isobutyryl and the like;
said halogen is fluorine, chlorine, or bromine.

The present invention provides a compound of formula 1 or a pharmaceutically acceptable salt thereof.

The term "pharmaceutically acceptable salt" as used in the present invention refers to, within the range of reliable medical evaluation, the salt of the compound is suitable to contact tissues of a human or lower animals without undue toxicity, irritation and allergy etc., has a reasonable benefit/risk ratio, is generally soluble or dispersible in water or oil, and is effective for their intended use. The salts which can be used herein and are compatible with the chemical property of the compound of formula 1 include pharmaceutically acceptable acid addition salts and pharmaceutically acceptable base addition salts.

The present invention also provides a process for the preparation of pyrazolo[1,5-a]pyrimidine derivatives as shown by formula 1.
1) When R$_2$=H, they are prepared according to the following scheme:

2

-continued

1

(1) To compound 2 is added dropwise 5M NaOH, stirred at 30-60° C. for 12 to 48 hours. Then to the solution is added dropwise 1M-3M HCl to adjust pH 3, subsequently extracted with ethyl acetate, dried over anhydrous sodium sulfate, filtered, evaporated to dryness to give a yellow oily liquid 4.

(2) Compound 4, N,N'-carbonyldiimidazole are dissolved in tetrahydrofuran, stirred at room temperature for 3-5 hours. Compounds potassium monoethyl malonate, anhydrous magnesium chloride and 4-dimethylaminopyridine are dissolved in acetonitrile and tetrahydrofuran, stirred at room temperature for 4-8 hours. The two reaction mixtures are cooled to 0° C. after they sufficiently react separately, then the above-mentioned first solution and triethylamine are simultaneously added to the second solution, and then stirred at room temperature overnight. After completion of the reaction, the solvent is removed by evaporation. The residue is diluted with water, extracted with ethyl acetate, dried over anhydrous sodium sulfate, filtered and evaporated to dryness to give a yellow oily liquid 5.

(3) Preparation of intermediate 6: Compound 61 and 62 are dissolved in a small amount of methylene chloride and the reaction is refluxed for 8-24 hours at 100° C. After cooling to room temperature, the reaction solution is added to a solution of hydrazine hydrochloride in 50% EtOH, refluxed overnight at 80° C. After completion of the reaction, it is then cooled to room temperature, basified with saturated NaHCO$_3$, extracted with ethyl acetate, washed with saturated brine, dried over anhydrous sodium sulfate, filtered and evaporated to dryness. Recrystallization with petroleum ether and ethyl acetate affords a white to pale yellow solid 6.

(4) Compounds 5 and 6 are dissolved in anhydrous ethanol. Trifluoroacetic acid is then added. The mixture is heated at 80° C. for 8-24 hours. After cooling to room temperature, the solvent is evaporated to dryness. The residue is diluted with water, adjusted to pH 8 with 1M NaOH, extracted with ethyl acetate, dried over anhydrous sodium sulfate, filtered, and evaporated to dryness. The residue is separated by silica gel column to give compound 7.

(5) Compound 7 is dissolved in methylene chloride. Trifluoroacetic acid is added at 0° C. The reaction is carried out at this temperature for 2-5 hours. The solvent is evaporated to dryness, and then the residue is adjusted to pH 10 with saturated sodium bicarbonate solution, filtered. The filter residue is washed with water and a small amount of ethyl acetate, dried in a vacuum drying oven to give 8 as a white solid.

(6) Compound 8 and a corresponding acid or acid chloride or an alkyl halohydrocarbon, 1-hydroxybenzotriazole, benzotriazole-N,N,N',N'-tetramethyluronium hexafluorophosphate are dissolved in DMF, stirred at room temperature. Diisopropyl ethyl amine is added. After reacting for 12 hours, the mixture is dissolved with ethyl acetate, washed with water, saturated brine, dried over anhydrous sodium sulfate, filtered, evaporated to dryness, purified by silica gel column to give compound 1 as a white solid.

2) When R$_2$≠H, compounds are prepared according to the following scheme:

(1) A round bottom flask is made free of water and oxygen. Diisopropylamine and THF are added under nitrogen atmosphere, then stirred at 0° C. To which is added 1.6M n-butyllithium dropwise at this temperature. After completion of the addition, the solution is stirred at 0° C. for 15-30 minutes and then placed at −78° C. To which is slowly added compound 2 dissolved in tetrahydrofuran. After stirring one hour, methyl iodide dissolved in tetrahydrofuran is added dropwise to the above solution. It was then allowed to warm to room temperature. After completion of reaction, the reaction is quenched with saturated ammonium chloride solution, evaporated to dryness, diluted with water, extracted with ethyl acetate, dried over anhydrous sodium sulfate, filtered, evaporated to dryness to give a brown oily liquid 3.

(2) To compound 3 is added dropwise 5M NaOH, stirred at 30-60° C. for 12 to 48 hours. And then to the solution is added dropwise 1M-3M HCl to pH 3, extracted with ethyl acetate, dried over anhydrous sodium sulfate, filtered, evaporated to dryness to give a yellow oily liquid 4.

(3) Compound 4, N,N'-carbonyldiimidazole are dissolved in tetrahydrofuran, stirred at room temperature for 3-5 hours. Compounds potassium monoethyl malonate, anhydrous magnesium chloride and 4-dimethylaminopyridine are dissolved in acetonitrile and tetrahydrofuran, stirred at room temperature for 4-8 hours. The two reaction mixtures are cooled to 0° C. after they sufficiently react separately, then the above-mentioned first solution and triethylamine are simultaneously added to the second solution, and then stirred overnight at room temperature. After completion of the reaction, the solvent is removed by evaporation. The residue is diluted with water, extracted with ethyl acetate, dried over anhydrous sodium sulfate, filtered and evaporated to dryness to give a yellow oily liquid 5.

(4) Preparation of intermediate 6: Compound 61 and 62 are dissolved in a small amount of methylene chloride and the reaction is refluxed for 8-24 hours at 100° C. After cooling to room temperature, the reaction solution is added to a solution of hydrazine hydrochloride in 50% EtOH, refluxed overnight at 80° C. After completion of the reaction, it is then cooled to room temperature, basified with saturated NaHCO$_3$, extracted with ethyl acetate, washed with saturated brine, dried over anhydrous sodium sulfate, filtered and evaporated to dryness. Recrystallization with petroleum ether and ethyl acetate affords a white to pale yellow solid 6.

(5) Compounds 5 and 6 are dissolved in anhydrous ethanol. Trifluoroacetic acid is then added. The mixture is heated at 80° C. for 8-24 hours. After cooling to room temperature, the solvent is evaporated to dryness. The residue is diluted with water, adjusted to pH 8 with 1M NaOH, extracted with ethyl acetate, dried over anhydrous sodium sulfate, filtered, and evaporated to dryness. The residue is separated by silica gel column to give compound 7.

(6) Compound 7 is dissolved in methylene chloride. Trifluoroacetic acid is added at 0° C. The reaction is carried out at this temperature for 2-5 hours. The solvent is evaporated to dryness, and then the residue is adjusted to pH 10 with saturated sodium bicarbonate solution, filtered. The filter residue is washed with water and a small amount of ethyl acetate, dried in a vacuum drying oven to give 8 as a white solid.

(7) Compound 8 and a corresponding acid or acid chloride or an alkyl halohydrocarbon, 1-hydroxybenzotriazole, benzotriazole-N,N,N',N'-tetramethyluronium hexafluorophosphate are dissolved in DMF, stirred at room temperature. Diisopropyl ethyl amine is added. After reacting for 12 hours, the mixture is dissolved with ethyl acetate, washed with water, and saturated brine, dried over anhydrous sodium sulfate, filtered, evaporated to dryness, purified by silica gel column to give compound 1 as a white solid.

In the present invention, some particularly preferred compounds have the following structures:

M-085

M-086

-continued

EXAMPLES

The following examples are helpful to understand the present invention, but they cannot be explained as limiting the scope of the present invention.

Example 1

$R_1$=—COCHPh$_2$, $R_2$=H, $R_3$=F (1) To compound 2 (24.33 g, 0.1 mol) was added dropwise 5M NaOH (60 mL, 0.3 mol), then stirred at 50° C. for 24 hours. 3M HCl was then added dropwise to the solution to adjust pH 3. The mixture was extracted with ethyl acetate (3*200 mL), dried over anhydrous sodium sulfate, filtered, evaporated to dryness to give a yellow oily liquid 4 (19.72 g, 96%)

(2) Compound 4 (14.56 g, 63.5 mmol), N,N'-carbonyldiimidazole (24.00 g, 86 mmol) were dissolved in tetrahydrofuran (100 mL), stirred at room temperature for 4 hours. Compounds potassium monoethyl malonate (28.10 g, 165 mmol), anhydrous magnesium chloride (18.15 g, 191 mmol) and 4-dimethylaminopyridine (800 mg, 6.35 mmol) were dissolved in acetonitrile (100 mL) and tetrahydrofuran (200 mL), stirred at room temperature for 6 hours. The two reaction mixtures were cooled to 0° C. after they sufficiently reacted separately. Then the above-mentioned first solution and triethylamine (52 mL, 254 mmol) were simultaneously added to the second solution, and then stirred overnight at room temperature. After completion of the reaction, the solvent is removed by evaporation. The residue is diluted with water (200 mL), extracted with ethyl acetate (3*200 mL), dried over anhydrous sodium sulfate, filtered and evaporated to dryness to give a yellow oily liquid 5 (18.06 g, 95%).

(3) Preparation of intermediate 6: Compound 61 (21.6 mL), and 62 (21.9 mL) were dissolved in dichloromethane (10 mL). The reaction was refluxed for 24 hours at 100° C. After cooling to room temperature, the reaction solution was added to a solution of hydrazine hydrochloride in 50% EtOH (50 mL), refluxed at 80° C. overnight. After completion of the reaction, it was cooled to room temperature, basified with saturated NaHCO$_3$, extracted with ethyl acetate (3*100 mL), washed with saturated brine, dried over anhydrous sodium sulfate, filtered and evaporated to dryness. Recrystallization with petroleum ether and ethyl acetate afforded white solid 6 (21.2 g, 78%).

(4) Compound 5 (15 g, 45 mmol) and compound 6 (9.45 g, 49.5 mmol) were dissolved in anhydrous ethanol (400 mL). Trifluoroacetic acid (20 mL) was added. The mixture was heated at 80° C. for 12 hours, then the heat is stopped. After cooling to room temperature, the solvent was evaporated to dryness. The residue was diluted with water (100 mL), adjusted to pH 8 with 1M NaOH, extracted with ethyl acetate (3*200 mL), dried over anhydrous sodium sulfate, filtered, and evaporated to dryness. The residue was separated by silica gel column (methanol:dichloromethane=1:20) to give compound 7 (13.82 g, 72%).

(5) Compound 7 (6.18 g, 15 mmol) was dissolved in dichloromethane (100 mL). Trifluoroacetic acid (35 mL) was added at 0° C. The reaction was carried out at this temperature for 2 hours. The solvent was evaporated to dryness. And then the residue was adjusted pH 10 by saturated sodium bicarbonate solution, filtered. The filter residue was washed with water and a small amount of ethyl acetate, dried in a vacuum drying oven to give 8 as a white solid (4.50 g, 92%).

(6) Compound 8 (3.27 g, 10 mmol), diphenylacetic acid (2.55 g), 1-hydroxybenzotriazole (4.1 g, 30 mmol), benzotriazole-N,N,N',N'-tetramethyluronium hexafluorophosphate (11.4 g, 30 mmol) were dissolved in DMF (50 mL), stirred at room temperature. Diisopropylethyl amine (15.6 mL, 90 mmol) was added. After reacting for 12 hours, the mixture was diluted with ethyl acetate (300 mL), washed with water (4*200 mL), saturated brine (100 mL), dried over anhydrous sodium sulfate, filtered, evaporated to dryness, purified by silica gel column (dichloromethane:methanol=30:1) to give M114 as a white solid (2.97 g, 57%). $^1$H NMR (400 MHz, CD$_3$OD) δ=7.34-7.28 (q, 4H), 7.25-7.22 (t, J=14.5 Hz, 5H), 7.18-7.08 (m, 5H), 5.47-5.45 (d, J=7.6 Hz, 1H), 4.72-4.69 (d, J=13.2 Hz, 1H), 4.18-4.15 (d, J=13.2 Hz, 1H), 3.28-3.27 (t, J=3.2 Hz, 1H), 3.00-2.94 (t, J=25 Hz, 1H), 2.83-2.77 (t, J=24 Hz, 1H), 2.66-2.60 (t, J=24 Hz, 1H), 1.95-1.92 (d, J=12.4 Hz, 1H), 1.72-1.69 (d, J=12.4 Hz, 1H), 1.55-1.47 (m, 1H), 1.15-1.06 (m, 1H). $^{13}$C NMR (101 MHz, CD$_3$OD) δ=172.5, 141.2, 140.9, 131.8, 131.8, 130.3, 129.7, 129.4, 128.2, 127.9, 115.9, 115.7, 55.7, 47.7, 44.7, 44.0, 32.7, 32.5, 14.0.

Example 2

R$_1$=—COOCH$_2$Ph, R$_2$=—CH$_3$, R$_3$=Cl, the procedures were the same as those in Example 1, except that R$_3$ is Cl instead of F. The resulting white solid was M121 (yield 69%). $^1$H NMR (400 MHz, (CD$_3$)$_2$SO) δ=7.94-7.90 (m, 2H), 7.39-7.31 (m, 7H), 5.44 (s, 1H), 5.10 (s, 2H), 4.13-4.10 (d, J=13.0 Hz, 2H), 2.91 (s, 2H), 2.63-2.56 (m, 1H), 2.47 (s, 3H), 1.85-1.82 (d, J=11.6 Hz, 2H), 1.67-1.60 (m, 2H). $^{13}$CNMR (101 MHz, (CD$_3$)$_2$SO) δ=165.5, 158.4, 154.5, 149.2, 147.5, 137.1, 134.4, 128.4, 128.2, 127.8, 127.8, 127.7, 127.5, 101.5, 90.5, 66.1, 43.9, 43.4, 31.2, 15.3.

Example 3

R$_1$=—COOEt, R$_2$=—CH$_3$, R$_3$=—F (1) A 500 mL round bottom flask was free of water and oxygen. Diisopropylamine (16.8 mL, 120 mmol) was added into the flask under a nitrogen atmosphere, and dissolved in tetrahydrofuran (150 mL), stirred at 0° C. To which was added slowly 1.6M n-butyllithium (75 mL, 120 mmol) dropwise at this temperature. After the addition, the reaction was stirred at 0° C. for 15 minutes and then placed at −78° C. Compound 2 (24.3 g) dissolved in tetrahydrofuran (60 mL) was added slowly dropwise to the above solution. After stirring one hour, methyl iodide (9.38 mL, 150 mmol) dissolved in tetrahydrofuran (60 mL) was added dropwise to the above solution. It was allowed to warm slowly to room temperature. After completion of the reaction, the reaction was quenched with saturated ammonium chloride solution, evaporated to remove the solvent, diluted with water (250 mL), extracted with ethyl acetate (3*250 mL), dried over anhydrous sodium sulfate, filtered, and evaporated to dryness to give a brown oily liquid 3 (24.18 g, 94%).

(2) To compound 3 (20.58 g, 80 mol) was added dropwise 5M NaOH (80 mL, 0.4 mol). After stirring at 60° C. for 24 hours, to the solution was added dropwise 3M HCl to pH 3, extracted with ethyl acetate (3*200 mL), dried over anhydrous sodium sulfate, filtered, evaporated to dryness to give a yellow oily liquid 4 (17.91 g, 92%).

(3) Compound 4 (12.65 g, 52 mmol), N,N'-carbonyldiimidazole (19.2 g, 69 mmol) were dissolved in tetrahydrofuran (80 mL), stirred at room temperature for 4 hours. Compounds potassium monoethyl malonate (22.48 g, 13.2 mmol), anhydrous magnesium chloride (14.52 g, 15.28 mmol) and 4-dimethylaminopyridine (416 mg, 0.52 mmol) were dissolved in acetonitrile (80 mL) and tetrahydrofuran (150 mL), stirred at room temperature for 6 hours. Then the two reaction mixtures were cooled to 0° C. after they sufficiently react separately, the first solution above and triethylamine (41.6 mL, 203 mmol) were simultaneously added to the second solution, and then stirred at room temperature overnight. After completion of the reaction, the solvent is removed by evaporation. The residue was diluted with water (150 mL), extracted with ethyl acetate (3*150 mL), dried over anhydrous sodium sulfate, filtered and evaporated to dryness to give a yellow oily liquid 5 (14.99 g, 93%).

(4) The preparation of intermediate 6 was as described in Example 1 (3)

(5) Compound 5 (12.54 g, 40 mmol) and compound 6 (8.41 g, 44 mmol) were dissolved in anhydrous ethanol (300 mL). Then trifluoroacetic acid (15 mL) was added. The mixture was heated at 80° C. for 12 hours. After cooling to room temperature, the solvent was evaporated to dryness. The residue was diluted with water (100 mL), adjusted pH 8 with 1M NaOH, extracted with ethyl acetate (3*200 mL), dried over anhydrous sodium sulfate, filtered, evaporated to dryness. The residue was separated by a silica gel column (methanol:dichloromethane=1:20) to give Compound 7 (12.69 g, 72%).

(6) Compound 7 (8.81 g, 20 mmol) was dissolved in dichloromethane (20 mL). Trifluoroacetic acid (40 mL) was added at 0° C., and reacted at this temperature for 2 hours. The solvent was evaporated. Then the residue was adjusted to pH 10 with saturated sodium bicarbonate solution, filtered. The filter residue was washed with water and a small amount of ethyl acetate, dried in a vacuum drying oven to give 8 as a white solid (6.18 g, 91%).

(7) Compound 8 (3.40 g, 10 mmol), ethyl chloroformate (1.15 mL), 1-hydroxybenzotriazole (4.1 g, 30 mmol), benzotriazole-N,N,N',N'-tetramethyluronium hexafluorophosphate (11.4 g, 30 mmol) were dissolved in DMF (50 mL), stirred at room temperature. Diisopropylethyl amine (15.6 mL, 90 mmol) was added. After reacting for 12 hours, the mixture was diluted with ethyl acetate (300 mL), washed with water (4*200 mL), saturated brine (100 mL), dried over anhydrous sodium sulfate, filtered, evaporated to dryness, purified on a silica gel column (dichloromethane:methanol=30:1) to give a white solid M110 (2.14 g, 52%) $^1$H NMR (400 MHz, CDCl$_3$) δ=9.84 (s, 1H), 7.16-7.13 (t, J=12.4 Hz, 2H), 6.93-6.88 (t, J=16.8 Hz, 2H), 5.70 (s, 1H), 4.10-4.05 (q, J=21.2 Hz, 2H), 3.60-3.58 (d, J=8 Hz, 2H), 3.47-3.43 (q, J=16.8 Hz, 2H), 2.14 (s, 5H), 1.75-1.74 (d, J=5.2 Hz, 2H), 1.45 (s, 3H), 1.25-1.21 (t, J=14 Hz). $^{13}$C NMR (101 MHz, CDCl$_3$) δ=162.7, 160.2, 157.1, 155.4, 151.5, 138.7, 131.2, 127.0, 115.1, 114.9, 103.4, 94.1, 61.4, 40.1, 37.7, 34.7, 29.7, 25.2, 14.6, 12.8.

Example 4

Figure 1:
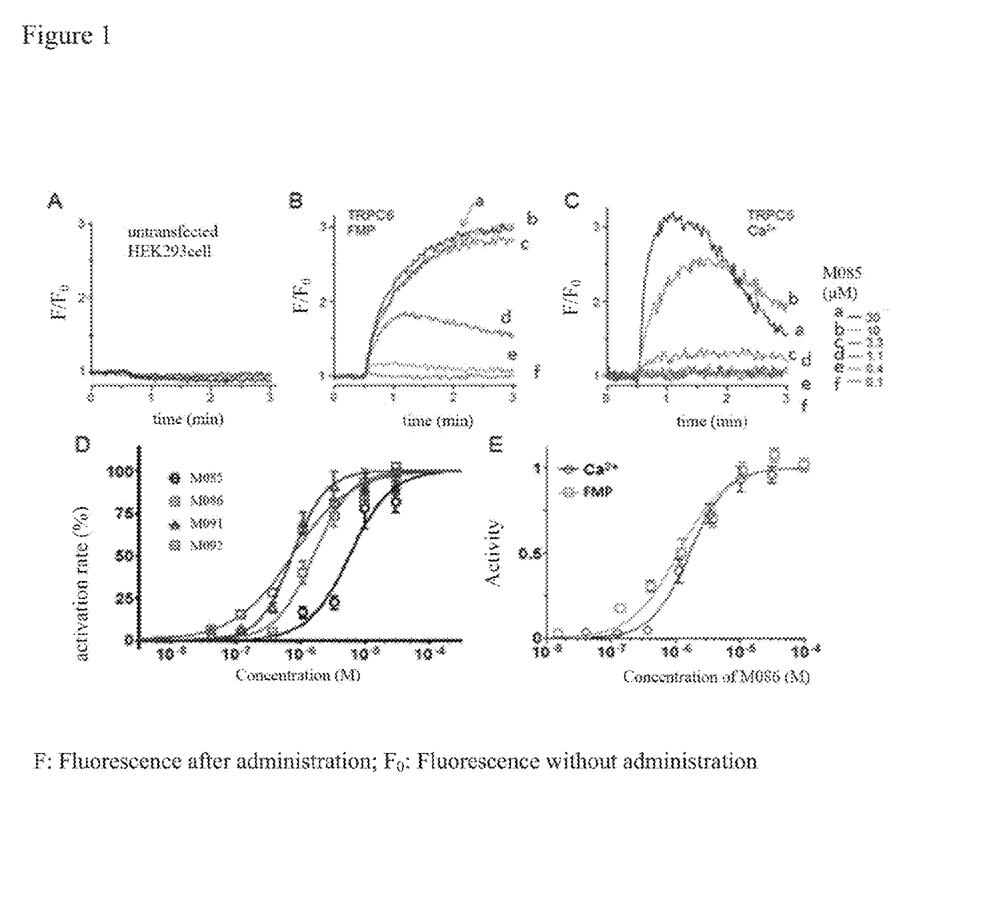
FIG. 1: The cell fluorescent membrane potential results of some compounds of the present invention to activate TRPC6 ion channel.

Cell Experiments of Some Compounds of the Present Invention (M085, M086, M091, M092) to Activate TRPC6 Ion Channels Pyrazolopyrimidines and their derivatives activated TRPC6 ion channels (FIG. 1). In HEK293 cells permanently transfected with TRPC6 ion channels, M085 was used as activator to detect the fluorescent membrane potential. Firstly, cells were stained with FLIPR membrane potential dyes (FMP). At 30 s, 0.1 μM, 0.4 μM, 1.1 μM, 3.3 μM, 10 μM, 30 μM of M085 were added, respectively. As for M085 at 0.4 μM~30 μM, the increased fluorescence in HEK293 cells permanently transfected with TRPC6 ion channels showed the increase of membrane depolarization (FIG. 1B). However, HEK293 cells which were not transfected with TRPC6 ion channels (control) showed no significantly fluorescent change (FIG. 1A).

Similar fluorescence calcium flux was used to detect the effect of M085 on [Ca$^{2+}$] concentration in HEK293 cells expressing mice TRPC6. The cells were stained using Ca$^{2+}$ indicator Fluo4. At 30 s, 0.1 μM, 0.4 μM, 1.1 μM, 3.3 μM, 10 μM, 30 μM of M085 were added. As for M085 at 3.3 μM~30 μM, intracellular [Ca$^{2+}$] significantly increased (FIG. 1C). The results of fluorescence calcium flux detection showed that, among the pyrazolopyrimidines and derivatives thereof, M085, M086, M091 and M092 exhibited activating effect for TRPC6 ion channel. The concentration response curve is shown in FIG. 1D. Wherein, M086 was subjected to fluorescent calcium flux detection and fluorescent membrane potential detection, respectively. The results are shown in FIG. 1E.

Figure 2:
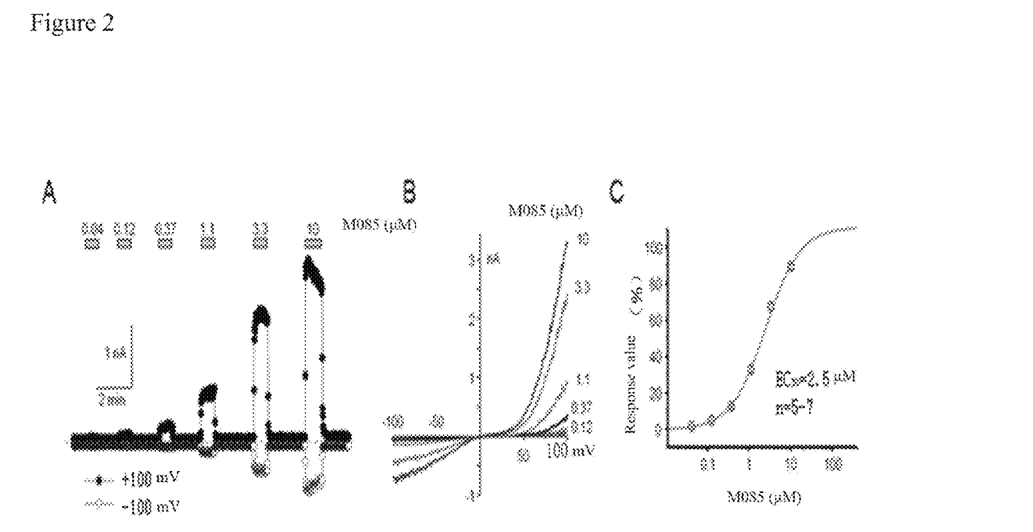
FIG. 2: The whole cell patch clamp test results of some compounds of the present invention to activate TRPC6 ion channel.

The whole-cell patch clamp assay showed the pyrazolopyrimidines and derivatives thereof (M085, M086, M091 and M092) have activation effect for TRPC6 channel (M085 is representative, FIG. 2A). HEK293 cells were clamped at −100~+100 mV in the whole-cell recording mode. At different concentrations (0.04 μM, 0.12 μM, 0.37 μM, 1.1 μM, 3.3 μM and 10 μM) M085 exhibited activation effect for TRPC6. The current-voltage relationship is shown in FIG. 2B. The concentration response curve is shown in FIG. 2C. EC$_{50}$=2.5 μM (n=5-7).

Example 5

Figure 3:
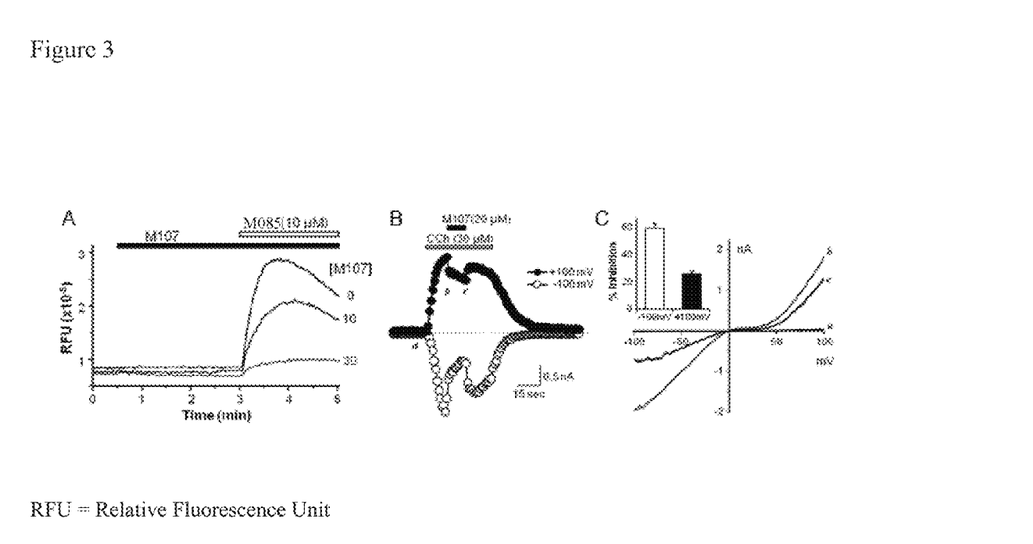
FIG. 3: The cell experiment result of some compounds of the present invention to block TRPC6 ion channel.

Cell Experiments of Some Compounds (M107, M110) of the Present Invention to Block TRPC6 Ion Channels The pyrazolopyrimidines and derivatives thereof (M107, M110) can block TRPC6 ion channels (FIG. 3). In HEK293 cells permanently transfected with M5 muscarinic receptors and TRPC6 ion channels, an agonist was used to activate the channels and detect fluorescence membrane potential. After the cells were treated with 0 μM, 10 μM, 30 μM of M107 for 3 min, 10 μM of M085 was added. The enhanced fluorescence intensity indicated the increases of membrane potential depolarization. While the membrane potential depolarization of cells treated by M107 was inhibited (FIG. 3A).

The whole-cell patch clamp assay showed the pyrazolopyrimidines and derivatives thereof (M107, M110) inhibited TRPC6 channel. M107 is representative (FIG. 3B, C). HEK293 cells were clamped at −100~+100 mV in whole-cell recording mode. TRPC6 ion channels activated by carbachol (CCh, 30 μM) was inhibited by M107 (20 μM). At −100~+100 mV, 20 μM of M107 provided 60% and 20% of inhibition rate for CCh (n=5).

Example 6

The Cytotoxic Activity Screening Test of the Compound of the Present Invention at Cellular Level After the cells in logarithmic growth phase were digested with 0.25% trypsin-EDTA, a cell suspension at a certain concentration was prepared. Depending on cell growth rate, they were inoculated in 96-well plates at 1000-2000 cells/well. To each well 100 μL of the cell suspension was added. After 24 h, fresh medium containing various concentrations of the compounds or the corresponding solvent were added at 100 μL per well (DMSO final concentration <0.1%). 5 to 7 dose groups were arranged for each test compound. Each group comprised at least 3 parallel wells. After further culturing at 37° C. for 72 h, the supernatant was discarded. 100 μL of fresh serum-free medium containing 0.5 mg/mL MTT was added to each well, further cultured for 2 h. After the supernatant was discarded, to each well was added 200 μL DMSO to dissolve MTT formazan precipitate. After mixing homogeneously by a microoscillator, optical density (OD) was measured at 450 nm of reference wavelength, and at 570 nm of detection wavelength by a Microplate reader. The tumor cells treated by the solvent control was used as the control group. The inhibition rate of tumor cells for the compounds were calculated by the following equation and IC$_{50}$ was calculated by the half of inhibition equation:

$$\text{Inhibition rate (\%)} = \frac{\text{the average } OD \text{ value of the control group} - \text{the average } OD \text{ value of the treated group}}{\text{the average } OD \text{ value of the control group}} * 100\%$$

(The results are shown in Table 1)

TABLE 1

The results of cytotoxic activity in vitro of some compounds of the present invention

| Cell lines | IC$_{50}$ (μM) M110 |
|---|---|
| MCF7 | 12.07 |
| H460 | 21.85 |
| KB | 9.47 |
| Lncap | 4.33 |
| Pc3 | 30.76 |
| Du145 | >100 |
| RM-1 | 25.64 |

MCF7 is human breast cancer cell line;
H460 is human lung cancer cell line;
Lncap, Pc3, Du145 is human prostate cancer cell lines;
KB is human oral epithelium carcinoma cell line;
RM-1 is mouse prostate cancer cell line.

Example 7

Animal Activity Experiments In Vivo of Compounds of the Invention

Male C57/BL6 mice (18-22 g) were used. The experiment procedures are summarized as follows: mice who had prostate cancer RM-1 and grown well were sacrificed by cervical dislocation. Under sterile conditions, tumor mass growing well was stripped off, homogenized, diluted with physiological saline in 1:4. Each mouse was inoculated 0.2 mL of the tumor solution in the armpit and back (approximately 2*10$^6$ cells). On the next day, the animals were randomized into groups and the administration began. Compound M110 was administered at 50 mg/kg by intraperitoneal injection at 24 h after inoculation. The dosing volume was 0.1 mL/10 g. At the same time, docetaxel control group and solvent control group were set. As for the docetaxel group, the animals were administered by intraperitoneal injection at 10 mg/kg dose, the dosing volume was 0.1 mL/10 g. After continuous administration for 10 days, the animals were sacrificed by cervical dislocation, weighed the body and the tumor, respectively. Inhibition rate of tumor growth (%) was calculated, and the results were statistically processed.

$$\text{Inhibition rate of tumor}(\%) = \frac{\text{average tumor weight of control group} - \text{average tumor weight of treatment group}}{\text{average tumor weight of control group}} * 100\%$$

TABLE 2

The effect of the invention compound on mice prostate cancer RM-1 transplanted tumor weight and body weight of the animals

| Group | dose (mg/kg) × d | body weight of Animals (g) Initial | body weight of Animals (g) Final | Tumor weight (g) | Inhibition rate |
|---|---|---|---|---|---|
| Control |  | 17.92 ± 1.07 | 21.50 ± 1.41 | 2.59 ± 0.47 |  |
| Docetaxel | 10 × 3 | 20.00 ± 1.07 | 18.43 ± 2.17 | 1.77 ± 0.61 | 32% |
| M110 | 50 × 4 | 20.00 ± 0.76 | 21.33 ± 1.51 | 2.0 ± 0.73 | 23% |

The above experimental results show that the compound M110 having the general formula according to the present invention has a pharmacological activity in vivo to inhibit growth of prostate cancer RM-1 transplanted tumor in mice.

The invention claimed is:

1. A pyrazolo[1,5-a]pyrimidine derivative or a pharmaceutically acceptable salt thereof, characterized in that the pyrazolo[1,5-a]pyrimidine derivative has the structure as shown in general formula 1:

wherein,
R$_1$ is hydrogen, alkylcarbonyl, alkoxycarbonyl, or alkylthiocarbonyl;
R$_2$ is monochloromethyl or trifluoroethyl; and
R$_3$ is hydrogen, halogen, or trifluoromethyl.

2. A composition comprising a pyrazolo[1,5-a]pyrimidine derivative or a pharmaceutically acceptable salt thereof according to claim 1, and a pharmaceutically acceptable carrier.

3. A method of treating breast cancer, lung cancer, prostate cancer or epithelial carcinoma comprising administering an effective amount of a pyrazolo[1,5-a]pyrimidine derivative or a pharmaceutically acceptable salt thereof according to claim 1 to a subject in need thereof.

* * * * *

UNITED STATES PATENT AND TRADEMARK OFFICE
CERTIFICATE OF CORRECTION

| | | |
|---|---|---|
| PATENT NO. | : 9,499,552 B2 | |
| APPLICATION NO. | : 14/719971 | |
| DATED | : November 22, 2016 | |
| INVENTOR(S) | : Hongbo Wang et al. | |

It is certified that error appears in the above-identified patent and that said Letters Patent is hereby corrected as shown below:

On the Title Page (73) Assignees: "Yanti University, Yanti" should read --Yantai University, Yantai--.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*